(12) United States Patent
Lin et al.

(10) Patent No.: US 9,649,294 B2
(45) Date of Patent: May 16, 2017

(54) GLUCAGON RECEPTOR ANTAGONIST COMPOUNDS, COMPOSITIONS CONTAINING SUCH COMPOUNDS AND METHODS OF USE

(71) Applicant: Merck Sharp & Dohme Corp., Rahway, NJ (US)

(72) Inventors: Songnian Lin, Holmdel, NJ (US); Libo Xu, Bridgewater, NJ (US); Emma R. Parmee, Doylestown, PA (US); Xibin Liao, Zionsville, IN (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/030,779

(22) PCT Filed: Oct. 30, 2014

(86) PCT No.: PCT/US2014/063021
§ 371 (c)(1),
(2) Date: Apr. 20, 2016

(87) PCT Pub. No.: WO2015/066252
PCT Pub. Date: May 7, 2015

(65) Prior Publication Data
US 2016/0250184 A1   Sep. 1, 2016

Related U.S. Application Data

(60) Provisional application No. 61/899,374, filed on Nov. 4, 2013.

(51) Int. Cl.
| | | |
|---|---|---|
| *A61K 31/404* | (2006.01) |
| *C07D 209/18* | (2006.01) |
| *A61K 45/06* | (2006.01) |
| *A61K 31/397* | (2006.01) |
| *A61K 31/4035* | (2006.01) |
| *C07D 209/20* | (2006.01) |

(52) U.S. Cl.
CPC .......... *A61K 31/404* (2013.01); *A61K 31/397* (2013.01); *A61K 31/4035* (2013.01); *A61K 45/06* (2013.01); *C07D 209/18* (2013.01); *C07D 209/20* (2013.01)

(58) Field of Classification Search
CPC .......................... A61K 31/404; C07D 209/20
USPC .......................................... 548/511; 514/415
See application file for complete search history.

(56) References Cited

U.S. PATENT DOCUMENTS

| | | | |
|---|---|---|---|
| 5,776,954 A | 7/1998 | de Laszlo et al. |
| 6,951,699 B2 | 10/2005 | Yata et al. |
| 7,687,534 B2 * | 3/2010 | Stelmach | C07D 209/18 514/415 |
| RE42,461 E | 6/2011 | Rosenblum et al. |
| 2007/0088071 A1 | 4/2007 | Kim et al. |
| 2007/0105930 A1 | 5/2007 | Parmee et al. |
| 2007/0203186 A1 | 8/2007 | Beeson et al. |
| 2008/0108620 A1 | 5/2008 | Brockunier et al. |
| 2009/0054506 A1 | 2/2009 | Liang et al. |
| 2009/0054662 A1 | 2/2009 | Tan et al. |
| 2009/0209564 A1 | 8/2009 | Kim et al. |
| 2011/0065634 A1 | 3/2011 | Greenlee et al. |
| 2011/0178007 A1 | 7/2011 | Stamford et al. |
| 2011/0251248 A1 | 10/2011 | Lin et al. |
| 2011/0281795 A1 | 11/2011 | Lin et al. |
| 2011/0301082 A1 | 12/2011 | Lin et al. |
| 2011/0312911 A1 | 12/2011 | Kats-Kagan et al. |

FOREIGN PATENT DOCUMENTS

| | | |
|---|---|---|
| WO | 9716442 | 5/1997 |
| WO | 9804528 | 2/1998 |
| WO | 9821957 | 5/1998 |
| WO | 9822108 | 5/1998 |
| WO | 9822109 | 5/1998 |
| WO | 9901423 | 1/1999 |
| WO | 9932448 | 7/1999 |
| WO | 0039088 | 7/2000 |
| WO | 0069810 | 11/2000 |
| WO | 0200612 | 1/2002 |
| WO | 0240446 | 5/2002 |
| WO | 03048109 | 6/2003 |
| WO | 03051357 | 6/2003 |
| WO | 03053938 | 7/2003 |
| WO | 03097619 | 11/2003 |
| WO | 2004002480 | 1/2004 |
| WO | 2004050039 | 6/2004 |
| WO | 2004056763 | 7/2004 |
| WO | 2004062663 | 7/2004 |
| WO | 2004069158 | 8/2004 |

(Continued)

OTHER PUBLICATIONS

Grover et al, Computational identification of novel natural inhibitors of glucagon receptor for checking type II diabetes mellitus, BMC Bioinformatics, Jul. 2014, 1-8, vol. 15, S16.
Handlon et al., Glucagon receptor antagonists for the treatment of type 2 diabetes, 226th ACS Natl Meeting, 2003, ABS 164, MEDI.
International Search Report and Written Opinion for PCT/USUS2014063021, mailed on Jan. 14, 2015, 12 pages.
Kurukulasuriya et al., Biaryl amide glucagon receptor antagonists, Bioorganic & Medicinal Chemistry Letters, 2004, 2047-2050, 14.

(Continued)

*Primary Examiner* — Kamal Saeed
*Assistant Examiner* — Janet L Coppins
(74) *Attorney, Agent, or Firm* — Anna L. Cocuzzo; Catherine D. Fitch

(57) ABSTRACT

Glucagon receptor antagonist compounds are disclosed which are of long duration of action. The compounds are useful for treating type 2 diabetes and related conditions. Pharmaceutical compositions and methods of treatment are also included.

9 Claims, No Drawings

(56) References Cited

FOREIGN PATENT DOCUMENTS

| | | |
|---|---|---|
| WO | 2005118542 | 12/2005 |
| WO | 2005121097 | 12/2005 |
| WO | 2005123668 | 12/2005 |
| WO | 2006086488 | 8/2006 |
| WO | 2006102067 | 9/2006 |
| WO | 2007106181 | 9/2007 |
| WO | 2007114855 | 10/2007 |
| WO | 2007120270 | 10/2007 |
| WO | 2007120284 | 10/2007 |
| WO | 2007123581 | 11/2007 |
| WO | 2007136577 | 11/2007 |
| WO | 2008042223 | 4/2008 |
| WO | 2010030722 | 3/2010 |
| WO | 2010080971 | 7/2010 |
| WO | 2010144664 | 12/2010 |
| WO | 2011037815 | 3/2011 |
| WO | 2011119541 | 9/2011 |
| WO | 2011119559 | 9/2011 |

OTHER PUBLICATIONS

Siu, et al, Structure of the human glucagon class B G-protein-coupled receptor, Nature, Jul. 2013, 444-451, vol. 499.

\* cited by examiner

GLUCAGON RECEPTOR ANTAGONIST COMPOUNDS, COMPOSITIONS CONTAINING SUCH COMPOUNDS AND METHODS OF USE

CROSS-REFERENCE TO RELATED APPLICATIONS

This application is a U.S. National Phase application under 35 U.S.C. §371 of PCT/US2014/063021, filed Oct. 30, 2014, which published as WO2015/066252 on May 7, 2015, which claims priority from U.S. provisional application No. 61/899,374 filed Nov. 4, 2013.

BACKGROUND OF THE INVENTION

The invention relates to glucagon receptor antagonist compounds, compositions containing such compounds and various methods of treatment relating to type 2 diabetes mellitus and related conditions.

Diabetes refers to a disease process derived from multiple causative factors and is characterized by elevated levels of plasma glucose (hyperglycemia) in the fasting or postprandial state. Elevated levels of plasma glucose can result in various symptoms, including impacted (blurry) vision, excessive thirst, fatigue, hunger, frequent urination and weight loss. Left untreated, hyperglycemia can lead to serious vision problems, sores and infections in the feet and skin, nerve damage, and cardiovascular complications.

Absolute or relative elevations in glucagon levels have been shown to contribute to the hyperglycemic state in some patients with type 1 or type 2 diabetes. Glucagon is a key hormonal agent that acts in concert with insulin to mediate homeostatic regulation of the amount of glucose in the blood. Glucagon primarily acts by stimulating certain cells (important among these are liver cells) to release glucose when blood glucose levels fall. The action of glucagon is opposite to that of insulin, which stimulates cells to take up and store glucose whenever blood glucose levels rise. Glucagon exerts its action by binding to and activating its receptor. Both in healthy control animals as well as in animal models of type 1 and type 2 diabetes, neutralization of the effect of circulating glucagon with selective and specific antibodies has resulted in reduction of the glycemic level. Mice with a homozygous deletion of the glucagon receptor exhibit increased glucose tolerance. Also, inhibition of glucagon receptor expression using antisense oligonucleotides ameliorates diabetic syndrome in db/db mice. These studies suggest that glucagon suppression or an action that antagonizes glucagon action could be a useful adjunct to conventional treatment of hyperglycemia in diabetic patients. The action of glucagon can be suppressed by providing an antagonist or an inverse agonist, e.g., substances that inhibit or prevent constitutive, or glucagon-induced, glucagon receptor-mediated responses.

Glucagon receptor antagonists have been disclosed in the art, see, e.g., WO 2008/042223. It would be useful to identify additional glucagon receptor antagonists and particularly glucagon receptor antagonists offering improved properties.

SUMMARY OF THE INVENTION

A compound which is:

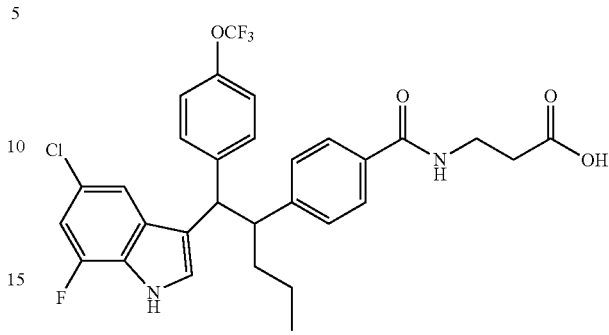

or a pharmaceutically acceptable salt thereof.

DETAILED DESCRIPTION OF THE INVENTION

The invention relates in particular to a compound of Formula I:

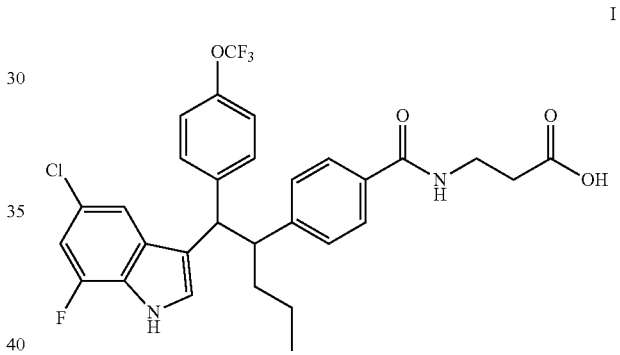

or a pharmaceutically acceptable salt thereof.

In particular embodiments, the compound is:

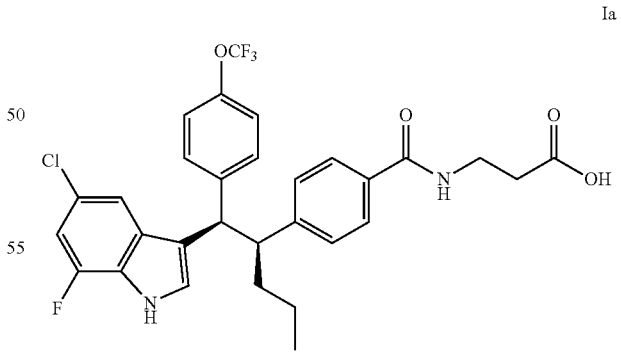

or a pharmaceutically acceptable salt thereof.

Compounds as disclosed are particularly desirable in that they exhibit a markedly longer half life in all 4 clinical species tested as compared with a previous lead molecule in the clinic. This finding was unexpected and provides effective glucagon receptor antagonist compounds of long duration of action.

Another aspect of the invention relates to a pharmaceutical composition comprising a compound of formula I or Ia as disclosed herein in combination with a pharmaceutically acceptable carrier.

Another aspect of the invention relates to a method of treating type 2 diabetes mellitus in a mammalian patient in need of such treatment comprising administering to said patient a compound of formula I or Ia as disclosed herein in an amount that is effective to treat type 2 diabetes mellitus.

Another aspect of the invention relates to a method of delaying the onset of type 2 diabetes mellitus in a mammalian patient in need thereof, comprising administering to the patient a compound of formula I or Ia as disclosed herein in an amount that is effective to delay the onset of type 2 diabetes mellitus.

Another aspect of the invention relates to a method of treating hyperglycemia, diabetes or insulin resistance in a mammalian patient in need of such treatment which comprises administering to said patient a compound of formula I or Ia as disclosed herein in an amount that is effective to treat hyperglycemia, diabetes or insulin resistance.

Another aspect of the invention relates to a method of treating non-insulin dependent diabetes mellitus in a mammalian patient in need of such treatment comprising administering to the patient an anti-diabetic effective amount of a compound of formula I or Ia as disclosed herein.

Another aspect of the invention relates to a method of treating a condition selected from the group consisting of: (1) hyperglycemia, (2) low glucose tolerance, (3) insulin resistance, (4) retinopathy, (5) nephropathy, (6) neuropathy, (7) Syndrome X, and other conditions and disorders where insulin resistance is a component, in a mammalian patient in need of such treatment, comprising administering to the patient a compound of formula I or Ia as disclosed herein in an amount that is effective to treat said condition.

Another aspect of the invention relates to a method of delaying the onset of a condition selected from the group consisting of (1) hyperglycemia, (2) low glucose tolerance, (3) insulin resistance, (4) retinopathy, (5) nephropathy, (6) neuropathy, (7) Syndrome X, and other conditions and disorders where insulin resistance is a component in a mammalian patient in need of such treatment, comprising administering to the patient a compound of formula I or Ia as disclosed herein in an amount that is effective to delay the onset of said condition.

Another aspect of the invention relates to a method of reducing the risk of developing a condition selected from the group consisting of (1) hyperglycemia, (2) low glucose tolerance, (3) insulin resistance, (4) retinopathy, (5) nephropathy, (6) neuropathy, (7) Syndrome X, and other conditions and disorders where insulin resistance is a component in a mammalian patient in need of such treatment, comprising administering to the patient a compound of formula I or Ia as disclosed herein in an amount that is effective to reduce the risk of developing said condition.

Another aspect of the invention relates to use of the compound of formula I or Ia as disclosed herein in the manufacture of a medicament for use in treating one ore more of the above-noted conditions.

Another aspect of the present invention relates to use of the compound of formula I or Ia as disclosed herein in therapy.

Optical Isomers—Diastereomers—Geometric Isomers—Tautomers

Compounds disclosed herein contain one or more asymmetric centers and thus occur as racemates and racemic mixtures, single enantiomers, diastereomeric mixtures and individual diastereomers. The invention includes all such isomeric forms of the compounds, in pure form as well as in mixtures.

Some of the compounds described herein may exist with different points of attachment of hydrogen, referred to as tautomers. Such an example may be a ketone and its enol form known as keto-enol tautomers. The individual tautomers as well as mixtures thereof are encompassed with the compounds disclosed herein.

Salts and Solvates

Salts and solvates of compounds of the compounds disclosed herein are included in the invention. The term "pharmaceutically acceptable salts" refers to salts prepared from pharmaceutically acceptable substantially non-toxic bases or acids including inorganic or organic bases and inorganic or organic acids, as well as salts that can be converted into pharmaceutically acceptable salts. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like.

Specific salts of the present invention are citric, hydrobromic, hydrochloric, maleic, phosphoric, sulfuric, and tartaric acids.

Solvates as used herein refers to the compound disclosed herein or a salt thereof, in association with a solvent, such as water. Representative examples include hydrates, hemihydrates, trihydrates and the like.

References to the compounds as disclosed herein are intended to include the pharmaceutically acceptable salts and solvates.

This invention relates to a method of inhibiting the activity of glucagon by antagonizing the glucagon receptor, thereby reducing the rate of gluconeogenesis and glycogenolysis, and the concentration of glucose in plasma.

The compounds as disclosed herein can be used in the manufacture of a medicament for the prophylactic or therapeutic treatment of disease states in mammals associated with elevated levels of glucose, comprised of combining the compound disclosed herein with the carrier materials to provide the medicament.

Dose Ranges

The prophylactic or therapeutic dose of a compound of formula I or Ia as disclosed herein will, of course, vary with the nature or severity of the condition to be treated, the particular compound selected and its route of administration. It will also vary according to the age, weight and response of the individual patient. In general, the daily dose range lies within the range of from about 0.001 mg to about 7 g per kg body weight, preferably about 0.01 mg to about 3.5 g per kg, and more preferably 0.1 to 10 mg per kg, in single or divided doses. It may be necessary to use dosages outside of these limits in some cases. The terms "effective amount", "anti-diabetic effective amount" and the other terms appearing throughout the application addressing the amount of the compound to be used refer to the dosage ranges provided, taking into account any necessary variation outside of these ranges, as determined by the skilled physician.

Representative dosages of compounds disclosed herein, as well as the pharmaceutically acceptable salts and solvates thereof, for adults range from about 0.1 mg to about 1.0 g per day, preferably about 1 mg to about 500 mg, in single or divided doses. Examples of suitable dosages include 0.1 mg, 1 mg, 2 mg, 5 mg, 10 mg, 20 mg, 40 mg, 50 mg, 75 mg, 100 mg, 150 mg, 200 mg, 250 mg, 500 mg, 1000 mg and similar such doses. Representative dosages of compounds used in combination with the compounds disclosed herein are known, or the determination thereof is within the level of skill in the art, taking into account the description provided herein.

When intravenous or oral administration is employed, a representative dosage range is from about 0.001 mg to about 7 g (preferably from 0.01 mg to about 0.7 g) of a compound disclosed herein per kg of body weight per day, and more preferably, about 0.1 mg to about 10 mg of a compound disclosed herein per kg of body weight per day.

When used in combination with other agents as further described below, the dosages noted above for the glucagon antagonist are provided along with the usual dose for the other medication. For example, when a DPP-IV inhibitor such as those disclosed in U.S. Pat. No. 6,699,871B1 is used in combination with a compound of formula I or Ia as disclosed herein, the DPP-IV inhibitor can be used in an amount ranging from about 1.0 mg to as high as about 1000 mg, preferably about 2.5 mg to about 250 mg, and in particular, about 50 mg or about 100 mg administered in single daily doses or in divided doses as appropriate. Similarly, when the glucagon receptor antagonist is used in combination with a CB1 antagonist/inverse agonist, the CB1 antagonist/inverse agonist can be used in an amount ranging from as low as about 0.1 mg to as high as about 1000 mg, more particularly, in an amount ranging from about 1.0 mg to about 100 mg, and even more particularly, in an amount from about 1.0 mg to about 10 mg, administered in single daily doses or in divided doses as appropriate. Examples of doses of CB1 antagonist/inverse agonist include 1 mg, 2 mg, 3 mg, 4 mg, 5 mg, 6 mg, 7 mg, 8 mg, 9 mg and 10 mg.

Pharmaceutical Compositions

As mentioned above, the pharmaceutical composition comprises a compound of formula I or Ia as disclosed herein or a pharmaceutically acceptable salt and/or solvate thereof and a pharmaceutically acceptable carrier. The term "composition" encompasses a product comprising the active and inert ingredient(s), (pharmaceutically acceptable excipients) that make up the carrier, as well as any product which results, directly or indirectly, from the combination, complexation or aggregation of any two or more of the ingredients, or from dissociation of one or more of the ingredients, or from other types of reactions or interactions between ingredients. Preferably the composition is comprised of a compound of formula I or Ia as disclosed herein in an amount that is effective to treat, prevent or delay the onset of type 2 diabetes mellitus, in combination with the pharmaceutically acceptable carrier.

Any suitable route of administration may be employed for providing a mammal, especially a human with an effective dosage of a compound of the invention. For example, oral, rectal, topical, parenteral, ocular, pulmonary, nasal, and the like may be employed. Examples of dosage forms include tablets, troches, dispersions, suspensions, solutions, capsules, creams, ointments, aerosols and the like, with oral tablets being preferred.

In preparing oral compositions, any of the usual pharmaceutical media may be employed, such as, for example, water, glycols, oils, alcohols, flavoring agents, preservatives, coloring agents and the like, in the case of oral liquids, e.g., suspensions, elixirs and solutions; or carriers such as starches, sugars, microcrystalline cellulose, diluents, granulating agents, lubricants, binders, disintegrating agents and the like in the case of oral solids, e.g., powders, capsules and tablets. Solid oral preparations are preferred. Because of their ease of administration, tablets and capsules represent the most advantageous oral dosage unit forms. If desired, tablets may be coated by standard aqueous or nonaqueous techniques.

In addition to the common dosage forms set out above, the compounds disclosed herein may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any acceptable pharmaceutical process. All such methods include the step of combining the active ingredient(s) with the carrier components. In general, the compositions are prepared by uniformly and intimately admixing the active ingredient(s) with a liquid or finely divided solid carrier component, and then, if necessary, manipulating the blend into the desired product form. For example, a tablet may be prepared by compression or molding. Compressed tablets may be prepared by compressing free-flowing powder or granules, containing the active(s) optionally mixed with one or more excipients, e.g., binders, lubricants, diluents, surfactants and dispersants. Molded tablets may be made by molding a mixture of the powdered compound moistened with an inert liquid. Desirably, each tablet may contain, for example, from about 0.1 mg to about 1.0 g of the active ingredient and each cachet or capsule contains from about 0.1 mg to about 500 mg of the active ingredient.

The following are examples of pharmaceutical dosage forms containing a compound of formula Ia as disclosed herein:

| INJECTABLE SUSPENSION (IM.) | MG/ML | TABLET | MG/TABLET |
|---|---|---|---|
| COMPOUND Ia | 10.0 | COMPOUND Ia | 25.0 |
| METHYLCELLULOSE | 5.0 | MICROCRYSTALLINE CELLULOSE | 415 |
| TWEEN 80 | 0.5 | POVIDONE | 14.0 |
| BENZYL ALCOHOL | 9.0 | PREGELATINIZED STARCH | 4.35 |
| BENZALKONIUM CHLORIDE | 1.0 | MAGNESIUM STEARATE | 2.5 |
| WATER FOR INJECTION | T.D. 1.0 ML | TOTAL | 500 MG |

| CAPSULE | MG/CAPSULE | AEROSOL | PER CANISTER |
|---|---|---|---|
| COMPOUND Ia | 25.0 | COMPOUND Ia | 250 MG |
| LACTOSE | 735 | LECITHIN, NF LIQ. CONC. | 1.2 MG |
| MG STEARATE | 1.5 | TRICHLOROMETHANE, NF | 4.025 G |
| TOTAL | 600 MG | DICHLORODIFLUOROMETHANE, NF | 12.15 G |

Combination Therapy

Compounds as disclosed herein may be used in combination with other drugs that are used in the treatment, prevention, suppression or amelioration of the diseases or conditions described above.

Accordingly, in particular embodiments the invention relates to a method of treating a condition selected from the group consisting of:

(1) hyperglycemia, (2) low glucose tolerance, (3) insulin resistance, (4) retinopathy, (5) nephropathy, (6) neuropathy, (7) Syndrome X, (8) other conditions and disorders where insulin resistance is a component, (9) hypercholesterolemia, (10) atherosclerosis, (11) low HDL levels, (12) high LDL levels, (13) hyperlipidemia, (14) hypertriglyceridemia and (15) dyslipidemia, in a mammalian patient in need of such treatment, comprising administering to the patient effective amounts of a compound of formula I or Ia as disclosed herein, and one or more compounds selected from the following paragraph.

Examples of other compounds (active ingredients) that may be combined with a compound of formula I or Ia as disclosed herein for the treatment or prevention of type 2 diabetes and the other conditions described herein, either administered separately or in the same pharmaceutical compositions, include, but are not limited to:

(1) dipeptidyl peptidase-IV (DPP-4) inhibitors (e.g., sitagliptin, alogliptin, linagliptin, vildagliptin, saxagliptin, teneligliptin, MK-3102);

(2) insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ dual agonists (e.g., ZYH2, ZYH1, GFT505, chiglitazar, muraglitazar, aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TTP814);

(3) insulin or insulin analogs (e.g., insulin detemir, insulin glulisine, insulin degludec, insulin glargine, insulin lispro, SB S1000 and oral and inhalable formulations of insulin and insulin analogs);

(4) leptin and leptin derivatives and agonists;

(5) amylin and amylin analogs (e.g., pramlintide);

(6) sulfonylurea and non-sulfonylurea insulin secretagogues (e.g., tolbutamide, glyburide, glipizide, glimepiride, mitiglinide, meglitinides, nateglinide and repaglinide);

(7) α-glucosidase inhibitors (e.g., acarbose, voglibose and miglitol);

(8) other glucagon receptor antagonists (e.g., NOXG15, LY2409021);

(9) incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, GSK2374697, ADX72231, RG7685, NN9924, ZYOG1, CJC-1131, and BIM-51077, including intranasal, transdermal, and once-weekly formulations thereof), and oxyntomodulin and oxyntomodulin analogs and derivatives;

(10) LDL cholesterol lowering agents such as (i) HMG-CoA reductase inhibitors (e.g., simvastatin, lovastatin, pravastatin, crivastatin, fluvastatin, atorvastatin, pitavastatin and rosuvastatin), (ii) bile acid sequestering agents (e.g., colestilan, colestimide, colesevalam hydrochloride, colestipol, cholestyramine, and dialkylaminoalkyl derivatives of a cross-linked dextran), (iii) inhibitors of cholesterol absorption, (e.g., ezetimibe), and (iv) acyl CoA:cholesterol acyltransferase inhibitors, (e.g., avasimibe);

(11) HDL-raising drugs, (e.g., niacin and nicotinic acid receptor agonists, and extended-release versions thereof; MK-524A, which is a combination of niacin extended-release and the DP-1 antagonist MK-524);

(12) antiobesity compounds;

(13) agents intended for use in inflammatory conditions, such as aspirin, non-steroidal anti-inflammatory drugs or NSAIDs, glucocorticoids, and selective cyclooxygenase-2 or COX-2 inhibitors;

(14) antihypertensive agents, such as ACE inhibitors (e.g., lisinopril, enalapril, ramipril, captopril, quinapril, and tandolapril), A-II receptor blockers (e.g., losartan, candesartan, irbesartan, olmesartan medoxomil, valsartan, telmisartan, and eprosartan), renin inhibitors (e.g., aliskiren), beta blockers, and calcium channel blockers;

(15) glucokinase activators (GKAs) (e.g., AZD6370);

(16) inhibitors of 11β-hydroxysteroid dehydrogenase type 1, (e.g., such as those disclosed in U.S. Pat. No. 6,730,690, and LY-2523199);

(17) CETP inhibitors (e.g., anacetrapib, evacetrapib or dalcetrapib);

(18) inhibitors of fructose 1,6-bisphosphatase, (e.g., such as those disclosed in U.S. Pat. Nos. 6,054,587; 6,110,903; 6,284,748; 6,399,782; and 6,489,476);

(19) inhibitors of acetyl CoA carboxylase-1 or 2 (ACC1 or ACC2);

(20) AMP-activated Protein Kinase (AMPK) activators, such as MB1055, ETC 1002;

(21) other agonists of the G-protein-coupled receptors: (i) GPR-109, (ii) GPR-119 (e.g., MBX2982, APD597, GSK1292263, HM47000, and PSN821), and (iii) GPR-40 (e.g., TAK875, CNX011, CNX 01162, CNX 01167, JTT 851, SAR1, MR 1704, TUG 770, TUG 469, TUG499, ASP 4178);

(22) SSTR3 antagonists (e.g., such as those disclosed in WO 2009/001836);

(23) neuromedin U receptor agonists (e.g., such as those disclosed in WO 2009/042053, including, but not limited to, neuromedin S (NMS));

(24) SCD inhibitors;

(25) GPR-105 antagonists (e.g., such as those disclosed in WO 2009/000087);

(26) SGLT inhibitors (e.g., ASP1941, SGLT-3, empagliflozin, dapagliflozin, canagliflozin, BI-10773, ertugliflozin, remogloflozin, TS-071, tofogliflozin, ipragliflozin, and LX-4211);

(27) inhibitors of acyl coenzyme A:diacylglycerol acyltransferase 1 and 2 (DGAT-1 and DGAT-2);

(28) inhibitors of fatty acid synthase;

(29) inhibitors of acyl coenzyme A:monoacylglycerol acyltransferase 1 and 2 (MGAT-1 and MGAT-2);

(30) agonists of the TGR5 receptor (also known as GPBAR1, BG37, GPCR19, GPR131, and M-BAR);

(31) ileal bile acid transporter inhibitors;

(32) PACAP, PACAP mimetics, and PACAP receptor 3 agonists;

(33) PPAR agonists;

(34) protein tyrosine phosphatase-1B (PTP-1B) inhibitors;

(35) IL-1b antibodies, (e.g., XOMA052 and canakinumab);

(36) bromocriptine mesylate and rapid-release formulations thereof; and

(37) GPR 120 agonists (such as KDT501), said compounds individually or collectively being administered to the patient in an amount that is effective to treat said condition.

According to this invention, it is to be understood that the above listed compounds also comprise their pharmaceutically acceptable salts as well as hydrates, solvates and polymorphic forms thereof.

Another aspect of the invention relates to a pharmaceutical composition comprising (1) a compound of formula I or Ia as disclosed herein; (2) any compound of use in a combination as described above, in combination with a pharmaceutically acceptable carrier.

The compounds may be administered by a route and in an amount commonly employed either contemporaneously or sequentially with a compound of formula I or Ia as disclosed herein. When a compound of formula I or Ia as disclosed herein is used contemporaneously with one or more other drugs, a pharmaceutical composition containing such other drugs in addition to the compound disclosed herein is preferred.

For combination products, the compound disclosed herein may be combined with any other active ingredients and then added to the carrier ingredients; alternatively the order of mixing may be varied.

The weight ratio of the compound of formula I or Ia as disclosed herein to the second active ingredient may be varied within wide limits and depends upon the effective dose of each active ingredient. Generally, an effective dose of each will be used. Thus, for example, when a compound of formula I or Ia as disclosed herein is combined with a PPAR agonist the weight ratio of the compound of formula I or Ia as disclosed herein to the PPAR agonist will generally range from about 1000:1 to about 1:1000, preferably about 200:1 to about 1:200. Combinations of a compound of formula I or Ia as disclosed herein and other active ingredients will generally also be within the aforementioned range, but in each case, an effective dose of each active ingredient should be used.

Another aspect of the invention relates to a method of treating a lipid disorder selected from the group consisting of dyslipidemia, hyperlipidemia, hypertriglyceridemia, hypercholesterolemia, low HDL and high LDL in a mammalian patient in need of such treatment, comprising administering to said patient a compound of formula I or Ia as disclosed herein in combination with a cholesterol lowering agent (included but not limited to HMG-CoA reductase inhibitors, bile acid sequestering agents, cholesterol absorption inhibitors and acyl CoA:cholesterol acyltransferase inhibitors) or other lipid altering agent including but not limited to HDL-raising agents in an amount that is effective to treat said lipid disorder.

Even more particularly, another aspect of the invention relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I or Ia as disclosed herein and an HMG-CoA reductase inhibitor, wherein the HMG-CoA reductase inhibitor is a statin selected from the group consisting of simvastatin, lovastatin, pravastatin, crivastatin, fluvastatin, atorvastatin, pitavastatin and rosuvastatin.

An additional aspect of the invention relates to a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient therapeutically effective amounts of a compound of formula I or Ia as disclosed herein and a cholesterol absorption inhibitor.

In specific embodiments, the invention relates to a method of treating diabetes or reducing hyperglycemia in a subject in need thereof having an LDL cholesterol plasma level of less than 130 mg/dL by administering a compound of formula I or Ia as disclosed herein in combination with a cholesterol absorption inhibitor.

The invention further relates in specific embodiments to a method for preventing one or more of the following conditions in a subject in need thereof having an LDL cholesterol plasma level of less than 130 mg/dL: (1) lipid disorders, (2) dyslipidemia, (3) hyperlipidemia, (4) hypertriglyceridemia, (5) hypercholesterolemia, (6) low HDL levels, (7) high LDL levels, (8) atherosclerosis and its sequelae and (9) vascular restenosis; which comprises administering a compound of formula I or Ia as disclosed herein in combination with a cholesterol absorption inhibitor to a subject having an LDL cholesterol plasma level of less than 130 mg/dL. An individual having diabetes or pre-diabetes is considered a subject in need thereof.

In particular embodiments of the methods and compositions of the invention, the subject has an LDL cholesterol plasma level of less than 120 mg/dL, less than 110 mg/dL, less than 100 mg/dL or less than 75 mg/dL.

In particular embodiments of the methods and compositions of the invention, the subject is further not being treated with a statin.

A "cholesterol absorption inhibitor" is defined herein as a compound able to prevent or reduce the uptake of cholesterol from the small intestine into the circulatory system. Cholesterol absorption inhibitors are effective in lowering the levels of total cholesterol and LDL cholesterol. The measurement of lipids is well known in the art including upon treatment with cholesterol absorption inhibitors, see, e.g., Dujovne et al., 2002 *Am. J. Cardiol.* 90(10):1092-1097. The invention is particularly directed to cholesterol absorption inhibitors having as a functional component thereof a small molecule compound, or in other words a low molecular weight organic compound. A small molecule is typically less than 800 Daltons.

The cholesterol absorption inhibitor in specific individual embodiments is selected from one of the following patent or scientific journal publication disclosures: U.S. Pat. No. RE 42,461; WO 07/59871; WO 07/47676; WO 06/86488; WO 05/123688; WO 05/121097; WO 06/14618; WO 08/42223; WO 08/98244; WO 2010/98948; US 20110306624; WO 2010/98994; WO 2010/88061; WO 2010/71750; WO 2010/30722; WO 06/104826; WO 05/65680; WO 06/102067; WO 06/17055; WO 2011/07722; WO 09/140342; or B. G. Salisbury et al., 1995 *Atherosclerosis* 115:45-63 and Burnett et al., 1994 *J. Med. Chem.* 137:733; although by no means limited thereto.

In specific embodiments, the cholesterol absorption inhibitor is ezetimibe:

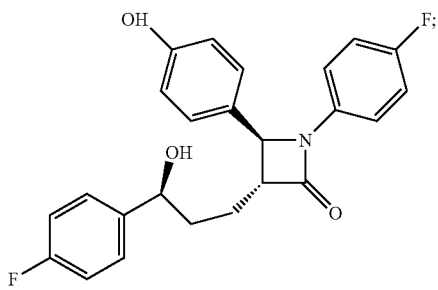 [SMILES: O=C1[C@H](CC[C@H](O)c2ccc(F)cc2)[C@@H](c2ccc(O)cc2)N1c1ccc(F)cc1]

or a pharmaceutically acceptable salt thereof. Ezetimibe is described, inter alia, in U.S. Pat. No. RE 42,461. Ezetimibe (Zetia®) can be prepared by a variety of methods well known to those skilled in the art, for example such as are disclosed in U.S. Pat. Nos. 5,631,365, 5,767,115, 5,846,966, 6,207,822 and PCT Patent Application WO 93/02048, each of which is incorporated herein by reference Another aspect of the invention relates to use of the compound of formula I or Ia as disclosed herein in combination with one or more other active ingredients in the manufacture of a medicament for use in treating one ore more of the above-noted conditions.

Another aspect of the invention relates to use of the compound of formula I or Ia as disclosed herein in combination with one or more other active ingredients in therapy.

EXAMPLES

The following examples are illustrative and provided so that the invention might be more fully understood. They should not be construed as limiting the invention in any way. The following abbreviations may be used in the Examples unless otherwise indicated:

BuLi, n-BuLi = n-butyllithium
CDI = carbonyl diimidazole
DCM = dichloromethane
DMSO = dimethyl sulfoxide
EDTA = ethylenediaminetetraacetic acid
EtOAc = ethyl acetate
IPA = isopropyl alcohol
LCMS, LC-MS = liquid chromatography - mass spectroscopy
Me = methyl
MeCN, $CH_3CN$ = acetonitrile
MeOH = methanol
$Na_2SO_4$ = sodium sulfate
PBS = phosphate buffer saline
$Pd_2(dba)_3$ = tris(dibenzylideneacetone)dipalladium(0)
Ph = phenyl
PTLC = preparative thin layer chromatography
PVT = polyvinyltoluene
TFA = trifluoroacetic acid
THF = tetrahydrofuran
TLC = thin layer chromatography
Tris-HCl = tris-hydrochloride
SPA = scintillation proximity assay
(S)-Tol-BINAP = (S)-(−)-2,2'-Bis(di-p-tolylphosphino)-1,1'-binaphthyl
WGA = wheat germ agglutinin Example 1

3-(4-((1R,2S)-1-(5-Chloro-7-Fluoro-1H-Indol-3-yl)-1-(4-(Trifluoromethoxy)Phenyl)Pentan-2-yl)Benzamido)Propanoic Acid

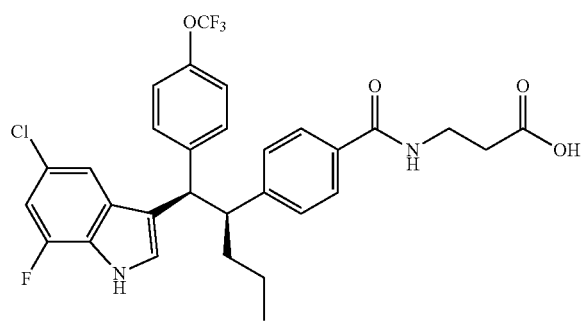 [SMILES: CCC[C@H](c1ccc(C(=O)NCCC(=O)O)cc1)[C@H](c1ccc(OC(F)(F)F)cc1)c1c[nH]c2c(F)cc(Cl)cc12]

Step A.
5-Chloro-7-fluoro-1-(phenylsulfonyl)-1H-indole

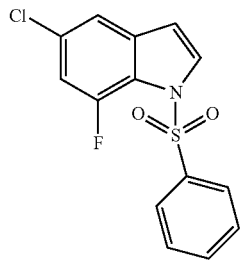 [SMILES: O=S(=O)(c1ccccc1)n1ccc2cc(Cl)cc(F)c21]

To a solution of 5-chloro-7-fluoro indole (500 mg, 2.95 mmol) in dry THF (30 ml) under $N_2$ at −78° C. (cooling bath) was added dropwise nBuLi (1.415 ml, 3.54 mmol). The cooling bath was then removed and the solution was stirred for 1 h while warming to 0° C. The resulting indole anion was cooled again to −78° C. Benzenesulfonyl chloride was added neat via syringe. The mixture was allowed to warm slowly to room temperature and stirred overnight. The mixture was poured into 2% aqueous sodium bicarbonate and extracted with EtOAc. The organic phase was dried over $Na_2SO_4$ and concentrated in vacuo. The residue was triturated with hexane and the resulting solid was collected by filtration and dried in vacuo.

Step B. Tert-butyl 4-(1-oxo-1-(4-(trifluoromethoxy)phenyl)pentan-2-yl)benzoate

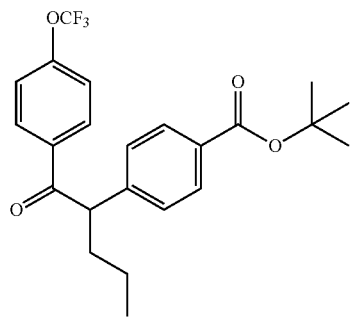 [SMILES: CCCC(C(=O)c1ccc(OC(F)(F)F)cc1)c1ccc(C(=O)OC(C)(C)C)cc1]

To a three-necked flask was charged with NaOtBu (11.6 g, 121.2 mmol) and 200 mL of dry THF, then $Pd_2(dba)_3$ (0.74 g, 0.81 mmol) and (S)-Tol-BINAP (1.9 g, 2.8 mmol) was added under nitrogen. The mixture was stirred at room temperature for 30 minutes, and 1-(4-(trifluoromethoxy)phenyl)butan-1-one (89 mmol) was added portion wise followed by tert-butyl 4-bromobenzoate (20.7 g, 80.8 mmol) under nitrogen. The suspension was refluxed overnight and then cooled to room temperature. The mixture was partitioned between water and EtOAc. The combined organic layers were washed with water and brine, dried over anhydrous $Na_2SO_4$ and concentrated. The residue was purified by column chromatography (eluted with petrol ether) and to afford title product $^1$H-NMR (CDCl3, 400 MHz) δ 7.97 (d, J=8.8 Hz, 2H), 7.91 (d, J=8.8 Hz, 2H), 7.32 (d, J=8.8 Hz, 2H), 7.19 (d, J=8.8 Hz, 2H), 4.54 (t, J=7.2 Hz, 1H), 2.11-2.19 (m, 1H), 1.76-1.83 (m, 1H), 1.55 (s, 9H), 1.22-1.33 (m, 2H), 0.91 (t, J=7.2 Hz, 3H).

Step C. Tert-butyl 4-((1R,2R)-1-hydroxy-1-(4-(trifluoromethoxy)phenyl)pentan-2-yl)benzoate

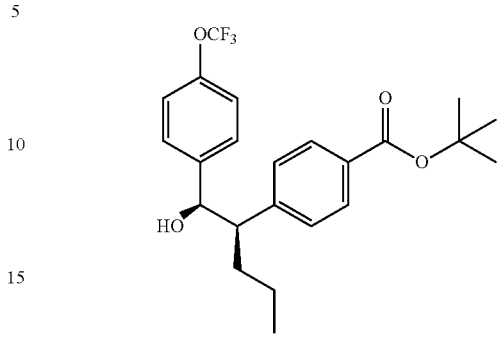

To 5 mL of degassed IPA was added potassium t-butoxide (516 mg, 4.6 mmol) and RuCl$_2$[(S)-xyl-SEGPHOS][(S)-DAIPEN] catalyst (28 mg, 0.023 mmol). The mixture was stirred at room temperature for 2 hrs before adding to a solution of tert-butyl 4-(1-oxo-1-(4-(trifluoromethoxy)phenyl)pentan-2-yl)benzoate (23 mmol) in 35 mL of IPA. This mixture was then hydrogenated under 100 psi of $H_2$ at room temperature overnight. Then IPA was removed and the residue was recrystalled with IPA/$H_2$O to afford the title compound. $^1$H-NMR (CDCl3, 300 MHz) δ 7.94 (d, J=8.8 Hz, 2H), 7.30 (d, J=8.8 Hz, 2H), 7.24 (d, J=8.8 Hz, 2H), 7.18 (d, J=8.8 Hz, 2H), 4.76 (t, J=8.0 Hz, 1H), 2.85-2.90 (m, 1H), 1.54-1.60 (m, 10H), 1.34-1.38 (m, 1H), 0.99-1.05 (m, 2H), 0.75 (t, J=7.2 Hz, 3H).

Step D. Ethyl 3-(4-((1R,2R)-1-hydroxy-1-(4-(trifluoromethoxy)phenyl)pentan-2-yl)benzamido)propanoate

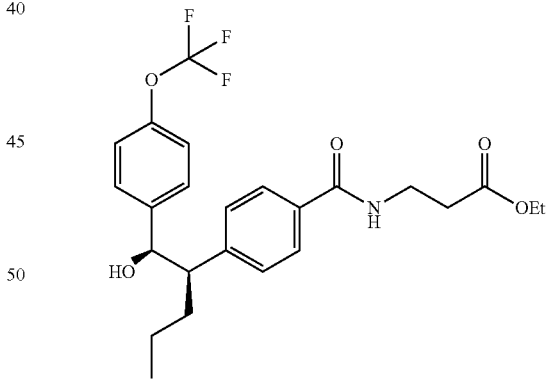

To a stirred solution of tert-butyl 4-((1R,2R)-1-hydroxy-1-(4-(trifluoromethoxy)phenyl)pentan-2-yl)benzoate (300 mg, 0.707 mmol) in MeCN (3.75 ml), was added phosphoric acid (0.243 ml, 3.53 mmol) and the mixture was stirred at 60° C. overnight. The reaction mixture was concentrated, and the residue was taken up in DCM and water. Organic layer was washed with water, dried over with sodium sulfate and concentrated to give the acid intermediate which was used without further purification. It was dissolved in THF (10 mL) and treated with CDI (227 mg, 1.4 mmol), followed by the addition of ethyl 3-aminopropanoate hydrochloride (122 mg, 0.797 mmol). The mixture was stirred at room temperature for 17 hours, diluted with EtOAc and washed with water. The organic layer was washed with water, dried over with sodium sulfate and concentrated. LCMS: 1.27 min, m/z 468.91.

Step E. Ethyl 3-(4-((1R,2S)-1-(5-chloro-7-fluoro-1-(phenylsulfonyl)-1H-indol-3-yl)-1-(4-(trifluoromethoxy)phenyl)pentan-2-yl)benzamido)propanoate

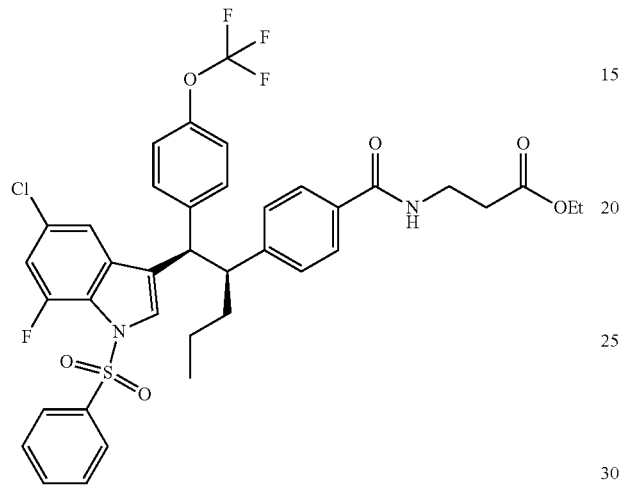

The product of Step A (50 mg, 0.146 mmol) and the product of Step D (82 mg, 0.175 mmol) were mixed in TFA (4 ml) and stirred overnight at room temperature. The mixture was concentrated and purified by preparative TLC to provide the product. LCMS: 2.64 min, m/z 759.40.

Step F. 3-(4-((1R,2S)-1-(5-chloro-7-fluoro-1H-indol-3-yl)-1-(4-(trifluoromethoxy)phenyl)-pentan-2-yl)benzamido)propanoic acid

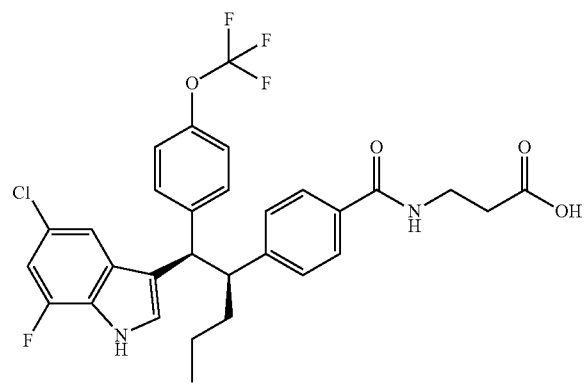 [SMILES: CCC[C@H](c1ccc(C(=O)NCCC(=O)O)cc1)[C@H](c1ccc(OC(F)(F)F)cc1)c1c[nH]c2c(F)cc(Cl)cc12]

To a solution of the product of Step E (16 mg, 0.021 mmol) in ethanol (1 ml) was added 2M aqueous solution of LiOH (0.25 ml, 0.500 mmol), and the reaction mixture was stirred at room temperature overnight. The mixture was then diluted with DCM and the pH was adjusted to 1 with 2N HCl. The phases were separated and the organic layer was concentrated. The crude residue was then purified by PTLC (DCM: MeOH=9:1) to afford the product. LCMS: 2.34 min, m/z 591.2. NMR 1H NMR (500 MHz, CD3OD): δ 0.71 (t, J=7.3 Hz, 3H); 1.02-1.00 (m, 2H); 1.51-1.48 (m, 2H); 2.58 (t, J=6.9 Hz, 2H); 3.31-3.30 (m, 1H); 3.56 (t, J=6.9 Hz, 2H); 4.52 (d, J=11.4 Hz, 1H); 6.74 (dd, J=10.7, 1.7 Hz, 1H); 7.21-7.20 (m, 3H); 7.28 (d, J=1.7 Hz, 1H); 7.36 (d, J=8.1 Hz, 2H); 7.58-7.56 (m, 4H).

Example 2

3-(4-((1S,2R)-1-(5-Chloro-7-Fluoro-1H-Indol-3-yl)-1-(4-(Trifluoromethoxy)Phenyl)Pentan-2-yl)Benzamido)Propanoic Acid

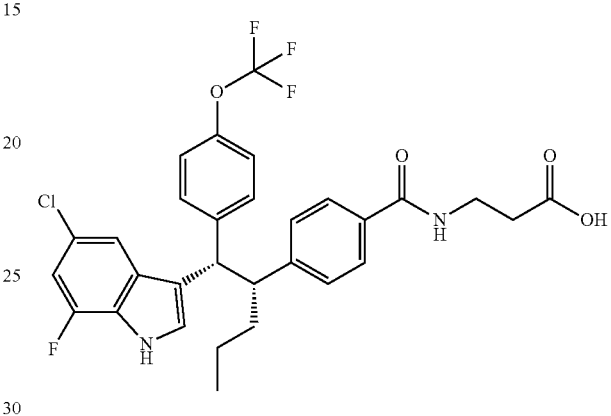

When RuCl$_2$[(R)-xyl-SEGPHOS][(R)-DAIPEN] is used in Step C of Example 1, the corresponding enantiomer, tert-butyl 4-((1S,2S)-1-hydroxy-1-(4-(trifluoromethoxy)phenyl)pentan-2-yl)benzoate, can be obtained. Following the same protocol as described in steps D-F in Example 1, the title compound can be obtained.

Example 3

3-(4-(1-(5-Chloro-7-Fluoro-1H-Indol-3-yl)-1-(4-(Trifluoromethoxy)Phenyl)Pentan-2-yl)Benzamido) Propanoic Acid

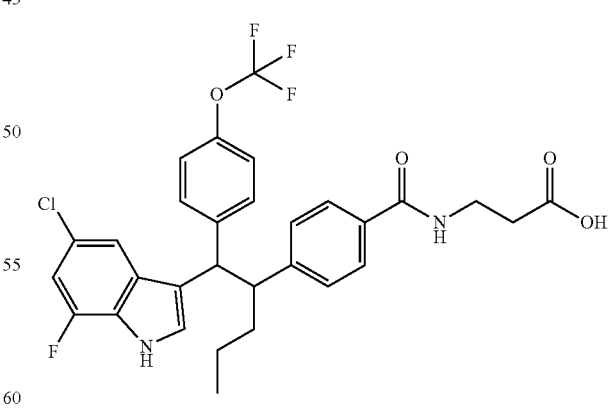

The product of Step B of Example 1 can be reduced with a common reducing agent such as NaBH$_4$, to afford a diasteromeric mixture of tert-butyl 4-(1-hydroxy-1-(4-(trifluoromethoxy)phenyl)pentan-2-yl)benzoate. Following the same protocol as described in steps D-F of Example 1, a racemic mixture of the title compound can be obtained.

Example 4

Biological Assays

The ability of a compound of the invention to inhibit the binding of glucagon and its utility in treating or preventing type 2 diabetes mellitus and the related conditions can be demonstrated by the following in vitro assays.

Glucagon Receptor Binding Assay

A stable CHO (Chinese hamster ovary) cell line expressing cloned human glucagon receptor was maintained as described (Chicchi et al. J Biol Chem 272, 7765-9(1997); Cascieri et al. J_Biol Chem 274, 8694-7(1999)). To determine antagonistic binding affinity of compounds 0.002 mg of cell membranes from these cells were incubated with $^{125}$I-Glucagon (New England Nuclear, MA) in a buffer containing 50 mM Tris-HCl (pH 7.5), 5 mM MgCl, 2 mM EDTA, 12% Glycerol, and 0.200 mg WGA coated PVT SPA beads (Amersham), +/−compounds or 0.001 MM unlabeled glucagon. After 4-12 hours incubation at room temperature, the radioactivity bound to the cell membranes was determined in a radioactive emission detection counter (Wallac-Microbeta). Data was analyzed using the software program Prism from GraphPad. $IC_{50}$ values were calculated using non-linear regression analysis assuming single site competition. An $IC_{50}$ value of 0.24 nM was obtained for the compound of the present invention, demonstrating utility as a glucagon antagonist.

Inhibition of Glucagon-Stimulated Intracellular cAMP Formation

Exponentially growing CHO cells expressing human glucagon receptor were harvested with the aid of enzyme-free dissociation media (Specialty Media), pelleted at low speed, and re-suspended in the Cell Stimulation Buffer included in the Flash Plate cAMP kit (New England Nuclear, SMP0004A). The adenylate cyclase assay was setup as per manufacturer instructions. Briefly, compounds were diluted from stocks in DMSO and added to cells at a final DMSO concentration of 5%. Cells prepared as above were preincubated in flash plates coated with anti-cAMP antibodies (NEN) in presence of compounds or DMSO controls for 30 minutes, and then stimulated with glucagon (250 pM) for an additional 30 minutes. The cell stimulation was stopped by addition of equal amount of a detection buffer containing lysis buffer as well as $^{125}$I-labeled cAMP tracer (NEN). After 3 hours of incubation at room temperature the bound radioactivity was determined in a liquid scintillation counter (TopCount-Packard Instruments). Basal activity (100% inhibition) was determined using the DMSO control while 0% inhibition was defined at the amount of pmol cAMP produced by 250 pM glucagon.

The compound of the present invention exhibited an IC50 of 19.2 nM, showing effective inhibition of glucagon-mediated function.

Example 5

Pharmacokinetic Studies

Intravenous (IV) PK studies were conducted at a dose of 1 mg/kg in hGCGR mice and rats and 0.5 mg/kg in dogs and rhesus monkeys. The IV doses were formulated in ethanol:PEG400:water (20:30:50 v/v/v). Oral PK studies were conducted at a dose of 2 mg/kg in mice, rats, dogs and monkeys. The oral doses were formulated in ethanol:PEG400:water (20:30:50 v/v/v) for dosing in mice and rats and in 0.5% methylcellulose in dogs and monkeys.

Plasma was prepared for analysis by protein precipitation with acetonitrile. Plasma concentrations were determined by LC-MS/MS using ABI Sciex API 4000 or 5000 mass spectrometers operated in atmospheric pressure chemical ionization mode with multiple-reaction monitoring.

Pharmacokinetic parameters were calculated with a non-compartmental model using Watson software (Watson Software, Thermo Fisher, Waltham, Mass., USA). The area under the plasma concentration versus time curve from 0 to 24 h ($AUC_{0-24}$) was determined using linear trapezoidal interpolation in the ascending slope and logarithmic trapezoidal interpolation in the descending slope. The portion of the AUC from the last measurable concentration to infinity ($AUC_{0-inf}$) was estimated by $Ct/k_{el}$, where Ct represents the last measurable concentration and $k_{el}$ is the elimination rate constant. The latter was determined from the concentration versus time curve at the terminal phase by linear regression of the semilogarithmic plot. Oral bioavailability (F) was estimated as the $AUC_{0-inf}$ ratio following oral and i.v. administration normalized for differences in dose. The apparent half-life (t1/2) was estimated from the slope of the terminal phase of the log plasma concentration-time curve. MRT, the average time a compound molecule resides in the body, is calculated with the following equation: MRT=AUMC/AUC. In this equation AUMC is the area under the first moment curve and is determined as the area under the curve of a plot of the product of concentration and time versus time. AUC is equal to $AUC_{0-inf}$.

Table 1 illustrates the results upon pharmacokinetic analysis of the compound of Example 1, 3-(4-((1R,2S)-1-(5-chloro-7-fluoro-1H-indol-3-YL)-1-(4-(trifluoromethoxy)phenyl)pentan-2-yl)benzamido)propanoic acid.

TABLE 1

| | Species | | | |
|---|---|---|---|---|
| PK parameter[b] | Mouse | Rat | Dog | Rhesus |
| $Cl_p$ (mL/min/kg) | 3.5 | 18 | 0.63 | 3.0 |
| $Vd_{ss}$ (L/kg) | 2.2 | 3.2 | 0.72 | 2.0 |
| $T_{1/2}$ (h) | 8.2 | 2.2 | 16 | 11 |
| MRT (h) | 10 | 2.9 | 20 | 11 |
| F (%) | 87 | 76 | 30 | 47 |
| Oral $AUC_{norm(0-\infty)}$ (μM · hr · kg/mg) | 8.0 | 1.2 | 16 | 6 |

[b]$Cl_p$, plasma clearance;
$Vd_{ss}$, volume of distribution at steady state;
$T_{1/2}$, terminal half-life; MRT, mean residence time;
F, oral bioavailability;
Oral AUC, dose-normalized area under the plasma concentration vs. time curve following oral dosing.

In comparison to the following lead molecule, the subject of clinical study "A Study of the Safety and Efficacy of MK3577 in Patients With Type 2 Diabetes Mellitus (Clinical Trial 473558)" described in U.S. Pat. No. 7,687,534:

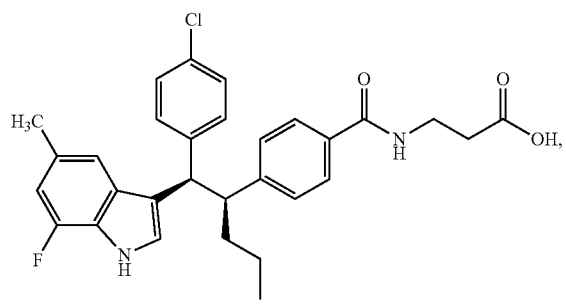 [SMILES: CCC[C@H](c1ccc(C(=O)NCCC(=O)O)cc1)[C@H](c1ccc(Cl)cc1)c1c[nH]c2c(F)cc(C)cc12]

the compound of the present invention exhibited markedly increased half-life across all four clinical species (mouse, rat, dog and rhesus monkey), enabling a molecule of long duration of action.

As shown in the Table 2 below, the compound of the present invention possesses ca 2.9-fold longer T1/2 in mouse compared to MK-3577, and its MRT in mouse was ca 4.5-fold that of MK-3577. In the rat, T1/2 for the compound of the present invention was ca 1.5-fold longer than MK-3577, while its MRT was over 3-fold compared to that of MK-3577. A similar trend was also observed in higher species such as dog and rhesus. T1/2 for the compound of the present invention was ca. 3.3-fold longer in dog and 2.2-fold longer in rhesus compared to MK-3577, while MRT was ca. 3.8-fold and 3.4-fold longer in dog and rhesus, respectively.

TABLE 2

|  | Mouse | | Rat | | Dog | | Rhesus | |
| --- | --- | --- | --- | --- | --- | --- | --- | --- |
|  | MK3577 | FORM I | MK3577 | FORM I | MK3577 | FORM I | MK3577 | FORM I |
| $T_{1/2}$ (h) | 2.8 | 8.2 | 1.4 | 2.2 | 4.9 | 16 | 5.1 | 11 |
| MRT (h) | 2.2 | 10 | 0.9 | 2.9 | 5.2 | 20 | 3.2 | 11 |

Certain embodiments of the invention have been described in detail; however, numerous other embodiments are contemplated as falling within the invention. Thus, the claims are not limited to the specific embodiments described herein. All patents, patent applications and publications that are cited herein are hereby incorporated by reference in their entirety.

What is claimed is:

1. A compound which is:

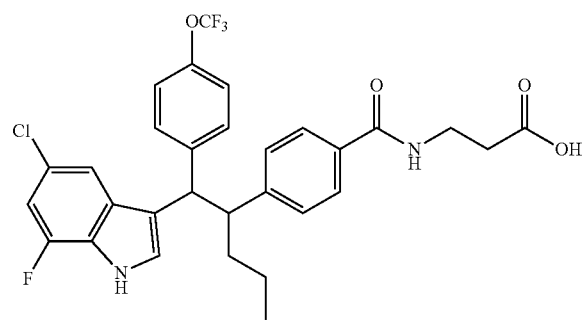 [SMILES: CCCC(c1ccc(C(=O)NCCC(=O)O)cc1)C(c1ccc(OC(F)(F)F)cc1)c1c[nH]c2c(F)cc(Cl)cc12]

or a pharmaceutically acceptable salt thereof.

2. The compound of claim 1 which is:

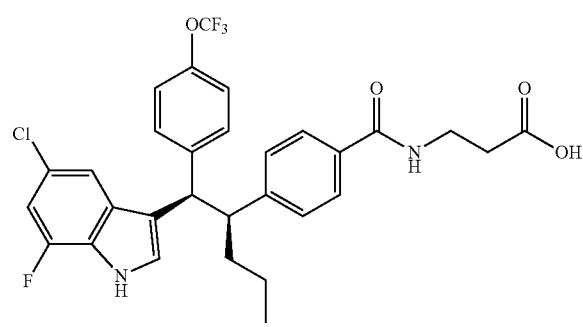 [SMILES: CCC[C@H](c1ccc(C(=O)NCCC(=O)O)cc1)[C@H](c1ccc(OC(F)(F)F)cc1)c1c[nH]c2c(F)cc(Cl)cc12]

or a pharmaceutically acceptable salt thereof.

3. A pharmaceutical composition comprising the compound of claim 1 or a pharmaceutically acceptable salt thereof in combination with a pharmaceutically acceptable carrier.

4. A method of treating type 2 diabetes mellitus in a mammalian patient in need of such treatment comprising administering to said patient the compound of claim 1 or a pharmaceutically acceptable salt thereof in an amount that is effective to treat said type 2 diabetes mellitus.

5. A method of treating hyperglycemia, diabetes or insulin resistance in a mammalian patient in need of such treatment which comprises administering to said patient an effective amount of the compound of claim 1 or a pharmaceutically acceptable salt thereof.

6. A method of treating a condition selected from the group consisting of: (1) hyperglycemia, (2) low glucose tolerance, (3) insulin resistance, (4) retinopathy, (5) nephropathy, (6) neuropathy, (7) Syndrome X, and other conditions and disorders where insulin resistance is a component, in a mammalian patient in need of such treatment, comprising administering to the patient the compound of claim 1 or a pharmaceutically acceptable salt thereof in an amount that is effective to treat said condition.

7. A method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient the compound of claim 1 or a pharmaceutically acceptable salt thereof in combination with a HMG-CoA reductase inhibitor.

8. A method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment, comprising administering to the patient the compound of claim 1 or a pharmaceutically acceptable salt thereof in combination with a cholesterol absorption inhibitor.

9. The method of claim 7 wherein the cholesterol absorption inhibitor compound is:

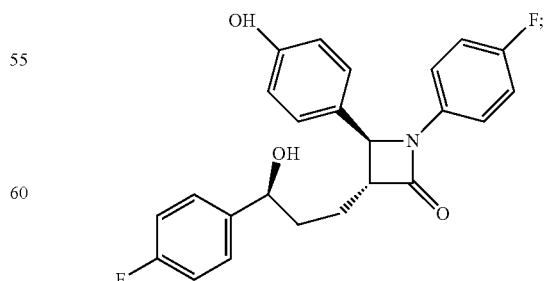

or a pharmaceutically acceptable salt thereof.

* * * * *